United States Patent [19]

Pennell et al.

[11] Patent Number: 4,983,585
[45] Date of Patent: Jan. 8, 1991

[54] VISCOELASTIC FLUID FOR USE IN SURGERY AND OTHER THERAPIES AND METHOD OF USING SAME

[75] Inventors: Phillip E. Pennell, Denver, Colo.; John M. Blackmore, Redwood City, Calif.; Mark D. Allen, Lakewood, Colo.

[73] Assignee: MDR Group, Inc., Golden, Colo.

[21] Appl. No.: 266,684

[22] Filed: Nov. 3, 1988

Related U.S. Application Data

[63] Continuation-in-part of Ser. No. 45,326, May 4, 1987, abandoned.

[51] Int. Cl.$^5$ .................. A61K 31/715; A61K 47/00
[52] U.S. Cl. .................................... 514/57; 514/781; 514/912; 514/915
[58] Field of Search .................. 424/631; 514/57, 781, 514/912, 915

[56] References Cited

U.S. PATENT DOCUMENTS 3,856,919 12/1974 Rankin .
3,947,573 3/1976 Rankin .

Primary Examiner—Stanley J. Friedman
Assistant Examiner—Zohreh A. Fay
Attorney, Agent, or Firm—Fliesler, Dubb, Meyer & Lovejoy

[57] ABSTRACT

This invention relates to an improved viscoelastic fluid or gel for use in surgery and other therapies which consists of polyethylene oxide in selected concentrations not to exceed approximately 15% (15,000 ppm), contained in a physiologic balanced salt solution. The PEO may also be used in conjunction with viscosity enhancers which also act as heat stabilizers such as methyl cellulose and its derivatives, polyvinyl pyrrolidone or polyvinyl, alcohol or in conjunction with elasticizers such as low molecular weight polyethylene glycols or polypropylene glycols or in conjunction with gelation modifiers. These mixtures may be modified to increase retention time in the body by crosslinking with the use of materials like dimethylol urea. The invention encompasses the novel method of protecting and lubricating the corneal tissues during surgery with uses of different concentrations of the same solution introduced simultaneously to protect the inner cornea while periodically irrigating the outer cornea, all without obscuring the surgeon's view of the site. This invention also prevents the development of wound adhesion and has many utilizations in orthopedics.

1 Claim, No Drawings

VISCOELASTIC FLUID FOR USE IN SURGERY AND OTHER THERAPIES AND METHOD OF USING SAME

CROSS-REFERENCE

This application is a Continuation-In-Part of co-pending application Ser. No. 07/045,326; Filed May 4, 1987, now abandoned.

BACKGROUND OF THE INVENTION

There are a number of ophthalmic musculoskeletal and nerve surgical procedures performed by skilled surgeons which require or are facilitated by the use of a viscoelastic medium. Among these are cataract surgery, vitreo-retinal surgery, radial keratotomy to reduce myopia, arthroscopic surgery, urologic surgery, joint surgery, plastic surgery, and wound adhesion prevention.

In all of the ophthalmic surgical procedures except for radial keratotomy in which the corneal tissue is not fully penetrated, the recommended practice is to use an intraocular viscoelastic fluid for protecting the inner endothelial corneal surface and the delicate inner eye structures.

In addition, the outer epithelial surface of the cornea must be lubricated continuously with some type of hydrating agent to keep it from drying out under the heat generated by the operating microscope light.

Methylcellulose has a long history of safe and effective use for ophthalmic applications. In 1945, Dr. Kenneth C. Swan studied the effects of methylcellulose on the ocular tissues of rabbit eyes. He suggested its use as a vehicle for ophthalmic drugs, to treat keratoconjunctivitis sicca and as an emollient. Then in 1959, Flemming, Merrill and Girard reported on further studies of methylcellulose in relation to irritation, hypersensitivity and its outflow from the anterior chamber of the rabbit eye.

The first reported use of methylcellulose as an intraocular lens coating serving to protect the corneal endothelium in rabbits was made by Drs. Kaufman and Katz in 1976. In the following year Dr. Paul Fechner reported upon the first human clinical use of methylcellulose to coat an intraocular lens prior to implantation.

Then in November of 1982, Dr. Danielle Aron-Rosa reported using methylcellulose in extracapsular surgery instead of high molecular weight sodium hyaluronate extracted from rooster combs which is very expensive. Shortly thereafter, Dr. Fechner amplified upon his earlier findings describing the use of methylcellulose as an intraocular viscous cushioning material in ophthalmic surgery.

Additional work confirming these earlier results has been conducted by Dr. Scott M. MacRae who compared the efficacy and toxicity of sodium hyaluronate, methylcellulose and chrondroitin sulfate, all three of which are used as protective substances suitable for use in ophthalmic surgery. Finally Drs. Smith and Lindstrom evaluated the safety and efficacy of 2% methylcellulose in cat and monkey implant surgery with favorable results.

As already noted, the use of methylcellulose derivatives as protective cushioning materials to protect the inner eye structures during ophthalmic surgery is old and well known. On the other hand, use of methylcellulose as one ingredient of a topical surgical solution which, in a more dilute form, is used to keep the corneal tissues moist as an adjunct to surgery is, once again, so far as applicant is aware, heretofore unknown in the art although it is, of course, used as an ingredient in so-called "artificial tears" for treating dry eyes and as a component of contact lens solutions.

The closest and most pertinent prior art known to applicant is contained in two U.S. Patents, specifically, U.S. Pat. No. 4,500,538 issued Feb. 19, 1985 to Otto W. Woltersdorf under the title of "Benzothiazolesulfonamide Derivatives for the Topical Treatment of Elevated Intraocular Pressure" and Irving Katz U.S. Pat. No. 4,287,175 issued Sept. 1, 1981 for "Contact Lens Wetting Agents", both of the aforementioned patents being assigned to Merck & Co., Inc. The earlier Katz patent teaches the use of hydroxypropylmethyl cellulose or polyethylene oxide among other polymeric viscosity building agents as a solid water soluble insert as a wetting agent for contact lens wearers or so-called "artificial tears". These wetting agents are, however, used in solid form and, as such, are totally unsuitable for use in hydrating and protecting the delicate epithelial cells in ophthalmic surgery. Moreover, there is no suggestion that they be used together or that any useful result whatsoever would be achieved by so doing. As a matter of fact, the elastic properties of the two in combination or, for that matter, either one alone is not a factor in their use as wetting agents.

The Woltersdorf patent also mentions the use of hydroxypropylmethyl cellulose and polyethylene oxide as solid water soluble carriers for the active medicament of the invention, namely, the carbonates of 6 or 5-hydroxy-2benzothiazolesulfonamide for use in the reduction of elevated intraocular pressure of the type often associated with glaucoma. Here again, these high molecular weight substances are used merely as a base for the active ingredient when used as a solid insert as opposed to a solution administered in the form of drops. There is no mention of them being used together nor is their elastic property of any consequence in this application. Most significant, however, is that the formulation of the Woltersdorf patent would be unsuitable for use as a viscoelastic coating to protect the delicate inner eye surfaces during opthalmic surgery or, for that matter, as a topical moisturizing agent to be used during such surgery as a long-lasting moisturizing agent.

In arthroscopy the surgeon visualizes the inside of a joint through a small diameter endoscope inserted into the joint through a 2 mm incision. The joint may upon through similar incisions using fiber-optic light systems along with miniaturized hand and motorized instruments.

Diagnostic arthroscopy is currently being used in temporomandibular, shoulder, elbow, wrist, finger, hip and ankle joints. Surgical arthroscopic procedures include synovectomy, chonodroplasty, removal of loose bodies and resection of scar tissue.

During the surgical procedures a copious flow of saline solution is used to maintain a clear surgical field. Intense, magnified light is directed into the surgical area through fiber-optic light bundles. During surgery the surgeon is assisted by a well trained technician. The technician helps to position the extremity, controls the irrigation system and hands instruments to the surgeon. Up to six liters of saline solution may be used during the procedure. The joint area is vacuumed to remove loose bodies and bloody synovial debris. Copious fluid flow and contact by the instruments to the bone may contribute to tissue damage and post surgical inflammation.

Modifications of sodium hyaluronate or hyaluronic acid are being developed to be used arthroscopic surgery to enhance visualization, and control bleeding; to be used as a post surgical joint lubricant to replace synovial fluid; and to be injected into joints to treat pain caused by arthritis. (Private Placement Memorandum for Biomatrix, Inc. by BNE Associates, June 14, 1988.)

Spinal laminectomies are performed when disc material extrudes from the spinal column, putting pressure on nerves, causing low back pain. The remedy is to remove the offending disc material. However, in nearly 70% of all spine surgery, while the surgery is successful, the pain is not eliminated and the patient suffers from "failed back syndrome". The cause for this failure is postulated to be scar tissue formation around the dura and nerve roots. Adhesions cause pressure and friction resulting in pain.

Methyl cellulose and methyl cellulose derivatives are known to reduce the formation of adhesions and scarring that may develop following surgery. (Thomas E. Elkins M.D., et al., "Potential for In-Vitro Growth Bacteria in Solutions of 32% Dextran 70 to 10% Sodium Carboxymethylcellulose" Fertility and Sterility, Vol. 43, #3, Mar. 1985; Thomas E. Elkins M.D., et al., "Adhesion Prevention by Solutions of Sodium Carboxymethylcellulose in The Rat, Part I", Fertility and Sterility, Vol. 41, #6, June 1984; Thomas E. Elkins M.D., et al., "Adhesion Prevention by Solutions of Sodium Carboxymethylcellulose in The Rat, Part II", Fertility and Sterility, Vol. 41, #6, June 1984; C. M. Federicks Ph.D., et al., "Adhesion Prevention in The Rabbit with Sodium Carboxymethylcellulose Solutions", American Journal of and Obstetrics and Gynecology, 1986; 1ss; 667.70).

Indwelling urinary catheters can be difficult to remove and the process painful to the patient. Mucous membranes tend to dry around the hydrophobic catheter. A dry coating which becomes slippery and stays hydrated would facilitate removal of catheters.

Urologic surgery is similar to arthroscopic surgery in the use of endscopic instruments, lights and large amounts of sterile saline operating fluids. Indeed, many of the techniques and devices of arthroscopy were derived from urologic procedures.

Implantable silicone prostheses are commonly used in plastic surgery. The silicone implants now on the market are filled with silicone gel or a saline solution. Saline solutions lack viscosity and in the event of implant rupture, they quickly lose their volume and shape. Silicone gel has been shown to permeate the silicone shell membrane with the result that the silicone fluid collects within the body. Silicone fluids are not broken down and excreted by the body and may cause adverse effects such as scleroderma. Post surgically, the body forms a scar around all silicone implants in a process known as capsular contracture. In mammary augmentation, this process results in firm, hard upraised breasts. The scar must be broken to restore a "natural"breast line. Adhesion formation is common with all types of silicone implants.

U.S. Pat. No. 4,042,978 to Jones et al. discloses the use of polyethylene oxide in a rigid plastic implantable prosthetic device.

Despite the high cost of viscoelastic products based upon sodium hyaluronate, all commercially available ones in common use have it as the sole or at least principal ingredient. Some manufacturers of viscoelastic materials have developed a bioengineered form of sodium hyaluronate but so far it appears that efforts at producing it with a sufficiently high molecular weight have been only marginally successful. A polyacrylamide based viscoelastic material is evidently being tested.

FIELD OF THE INVENTION

The present invention relates to an improved viscoelastic composition for use in surgery and other therapies as a lubricant, cushioning material, cellular protectant, visualization enhancer, bleeding controller, and an implantable prothesis. The invention, when used in various concentrations, has proven to be equally as good as, if not better than, sodium hyaluronate for use as a protective agent for the inner endothelial corneal surface and other delicate inner eye structures during ophthalmic surgery and considerably less expensive. Similar results have also been obtained with respect to orthopedics, urology, plastic, spinal and neurosurgery. The invention is also effective in the prevention of wound adhesion and scarring. The invention also encompasses the novel method of using the two different yet compatible solutions together during ophthalmic surgery so as to simultaneously protect the cornea and irrigate it without obscuring the surgeon's view of the site in any way.

SUMMARY OF THE INVENTION

The present invention is directed to the use of polyethylene oxide (PEO) containing viscoelastic fluids and/or gels primarily for use within extracellular normally sterile areas of the body of a patient. A normally sterile area means a part of the body that does not usually contain microorganisms.

The fluids or gels can contain up to 1.5% by weight of PEO (15000 ppm) and can be modified by the addition of any one or all of the following: viscosity enhancers which also serve as stabilizers to permit heat sterilization of fluids, elasticizers to increase the elasticity of the fluids and gelation modifiers which act as surface modifiers or surfactants.

The mixture is carried in an isotonic balanced salt solution resulting in a final pH of $7\pm0.2$ and a final osmolality of $320\pm40$.

The viscosity enhancers and stabilizers can include hydroxypropyl methylcellulose (HPMC), carboxymethyl cellulose (CMC), hydroxypropyl cellulose (HPC), hydroxyethyl cellulose (HEC), methyl cellulose (MC), or mixtures thereof. These polymers may make up from 0.5 to 3 weight percent of the final solution. Other viscosity enhancers can include polyvinyl pyrrolidone (0.5 to 3 weight percent) or polyvinyl alcohol (0.5 to 10 weight percent).

The elasticizers which can be added to the above mixtures or combinations thereof to increase elasticity include the lower molecular weight polyethylene glycols (up to 10,000 mw) and the lower molecular weight polypropylene glycols and trimethyol propane.

The gelation modifiers which can be added as surfactants to any of the above mixtures or combinations thereof include the Pluronic polyols F-127 and F-68.

The entire system can be modified to increase retention time in the body (that is, to prolong the absorption rate) by crosslinking with the use of materials like dimethylol urea, formaldehyde urea, formaldehyde or epichlorhydrin or other common crosslinking agents. The effect of this crosslinking is to bind OH radicals in a random manner between and among the materials.

This invention encompasses a novel fluid viscoelastic formulation of variable viscosity for use in ophthalmic surgery containing as its active ingredients a mixture of both hydroxypropylmethyl cellulose and polyethylene oxide together with a physiologic buffered saline solution. Other celluloses such as CMC, MC, HEC or HPC may also be used but HPMC is preferred. Hydroxypropylmethyl cellulose is clear, non-toxic and quite viscous, however, it is also essentially non-elastic. It has now been found in accordance with the teaching of the present invention that, quite unexpectedly, the addition of polyethylene oxide in small quantities (less than 500 ppm) which is a thixotropic material having a nominal molecular weight of 4 million, greatly improves the elasticity of the mixture and makes it comparable, if not superior, to sodium hyaluronate for use as a viscoelastic material in ophthalmic surgery. In addition, different relative concentrations of the two active ingredients in the aforesaid composition have proven to be far superior to balanced salt solution for topical application to keep the tissues moist during surgery by maintaining a smooth, hydrated cornea under the heat of the operating room microscope light. Moreover, since the two solutions contain the same active ingredients, they are fully compatible and can be used simultaneously to both protect and irrigate the delicate corneal tissues.

It is therefore the principal object of the present invention to provide a viscoelastic composition for use in extracellular normally sterile parts of a mammal's body comprising about 10 ppm to 15000 ppm PEO.

A second aspect is to provide a composition of the type aforementioned composition further comprising by weight 0.005% to 3% of a methyl cellulose.

Still another aspect of the invention herein disclosed is to provide compositions of the type aforementioned further comprising an elasticity modifier.

A still further aspect on the present invention is to provide a gelation modifier to the compositions of the type aforementioned.

Still yet another principal aspect of the present invention is to provide methods of treating patients using the aforementioned compositions.

It is also another aspect of the present invention to provide an improved viscoelastic solution for use in ophthalmic surgery which is made up in two different concentrations and administered simultaneously to both protect and irrigate the corneal tissues.

A further aspect is to provide a solution of the type aforementioned which is susceptible of being made up in selected viscosities by changing the relative concentrations of the active ingredients to adapt it for use as either a topical moisturizing agent or a protective shield for the delicate corneal surfaces and epithelial cells within the inner eye.

Still another objective of the invention herein disclosed and claimed is that of providing a topical moisturizing agent which remains effective many times longer than the conventional balanced salt solution while, at the same time, doing a better job.

Still yet another aspect of the within-described invention is to provide a protective solution for intracorneal use in eye surgery which has excellent clarity and transparency but, more importantly, much improved elasticity when compared with hydroxypropylmethyl cellulose alone.

An additional aspect is to provide a high-molecular weight viscoelastic mixture which is equally effective if not, in fact, superior to sodium hyaluronate-based products at a fraction of the cost.

Further aspects are to provide a solution for use in ophthalmic surgery which is safe, non-toxic, readily absorbed, easy to administer, versatile in its application, requires no refrigeration and has a long shelf life.

Other aspects will be in part apparent and in part pointed out specifically hereinafter in connection with the detailed description of the preferred embodiments which follow.

DESCRIPTION OF THE PREFERRED EMBODIMENTS

Ophthalmology

The anterior chamber of the eye is filled with circulating aqueous, whereas its posterior chamber with vitreous. The endothelial cell layer of the cornea is easily damaged and, once lost, these cells do not regenerate. The surgical procedures used in cataract surgery, corneal transplants and other types of ophthalmic surgery are likely to result in damage to these delicate cells unless measures are taken to protect them in the manner in which aqueous does naturally.

Of the several prior art substances that have been developed as substitutes for aqueous and vitreous, both as a protective layer covering the endothelial cells and as a coating on the surgical instruments and implanted material, undoubtedly the most widely used is sodium hyaluronate extracted from rooster combs, mixtures thereof or bioengineered forms of the naturally-occurring substance. Once the surgical procedure is completed, the remaining vitreous/aqueous substitute is aspirated from the site using a syringe while what is left over is merely resorbed by the body in time without ill effect.

The main problem with hyaluronate-based products is their cost which at the present time runs around $70 or so for less than one half of one cubic centimeter of material. While attempts have been made to use various methylcellulose derivatives as less expensive viscoelastic substitutes, they have not been well accepted nor do they work as well as hyaluronate.

It has now been found that a vastly improved material having greatly improved elasticity at least equivalent to sodium hyaluronate, but at a fraction of its cost, can be made by the simple, yet unobvious, expedient of combining the relatively non-elastic hydroxypropylmethyl cellulose with a high viscosity thixotropic elasticizer, specifically polyethylene oxide, both in a carrier comprising physiologic buffered saline solution.

The other problem encountered in ophthalmic surgery is that of keeping the external tissues of the eye moist under the drying effect of the operating microscope. As previously noted, this is generally handled on a more-or-less continuous basis by irrigating the external corneal tissues with a balanced salt solution, sometimes as often as twice a minute. Unexpectedly, applicant has discovered that a carefully modified mixture used as the intraocular viscoelastic material for the internal tissues can be advantageously used as a topical solution to keep the external corneal tissues moist many times longer than the balanced salt solution by merely varying the relative concentrations and, therefore, the resulting viscosity of the previously-mentioned intraocular viscoelastic solution that acts as a supplement and substitute for the naturally occurring aqueous fluid.

Specifically, the topical solution will contain approximately up to 1% hydroxypropylmethyl cellulose based on weight and from about 10 up to 40 ppm polyethylene oxide carried in the isotonic salt solution described above. This solution is used to hydrate the cornea for a prolonged period of time during surgery. By way of contrast, the intraocular viscoelastic composition will have the concentration of the hydroxypropylmethyl cellulose increased from about 2 to 2½% based on weight while the concentration of the polyethylene oxide remains the same. This solution is used as a surgical aid to increase visualization and to protect the sensitive internal eye structures during surgery. An alternative formulation is 2 weight percent CMC and 40 ppm PEO. An even more elastic intraocular fluid has high PEO (from about 50 to 500 ppm). This fluid is used to protect the corneal endothelial layer from high ultrasonic energy used during phacoemulsification of the nucleus in cataract surgery. In accordance with the teaching found herein, a unique method of simultaneously irrigating and protecting the delicate corneal tissues is taught using two fully compatible solutions containing the same active ingredients but in different concentrations. When this is done, the stroma and entire cornea are hydrated while the fluid loss through the incision is minimized. It also acts as a tamponade on the scleral flap area.

Since these fluids are aspirated from the eye upon completion of the surgery in order to minimize the incidence of intraocular pressure increases, a non-toxic and physiologically inert tinting material may be added so that the surgeon can be surer that he or she has removed most of the fluid added during the surgery. The resulting compositions, with or without the dye, have proven to be every bit as effective as hyaluronate-based preparations while being far less expensive and, at the same time, lowering operating room costs due to the more efficient use of personnel that results from the less frequent need for irrigation of the corneal tissues.

Orthopedics

The viscoelastic fluids of the invention may comprise a system of fluids which contain an operating fluid which facilitates the surgical process (a third pair of hands) and a cushioning fluid which enhances the patients recovery from surgery.

The operating fluid is used as a surgical aid. The fluid is injected into the joint and enhances visualization by the surgeon, the fluid coats and protects sensitive tissues from contact with the operating instruments and acts as a tamponade to control and direct bleeding. The fluid manipulates tissue during surgery and distends the joint capsule during surgery thereby reducing the amount of saline solution circulating through the joint during surgery. Copious fluid flow may contribute to tissue damage and post surgical inflammation.

In diagnostic and surgical arthroscopy the operating fluid can have from 20 to 1000 ppm of PEO (0.1/10 of 1 weight percent) in a 2 weight percent solution of HPMC.

Arthroscopic examination is made on two of the knees of the 10 dogs.

The knee joints of half of these dogs are injected with 1.0 ml of a 1000 ppm PEO and 2 weight percent HPMC solution during the surgery. The joints of the other half of the dogs are injected with 1.0 ml of a physiological saline solution as a control. Better visibility, less bleeding and debris are observed in the animals receiving the viscoelastic fluid than the control. The viscoelastic inflates the joint capsule during surgery. Minimal post operative inflammation is observed.

The viscoelastic cushioning fluid acts as a cushioning barrier between hard joint surfaces during the immediate post-surgical period before the synovial fluid has had a chance to be replaced naturally as well as to act as a replacement synovial fluid for a short period of time. It reduces postsurgical inflammation by creating less friction within the joint and acts as a joint lubricant. It also reduces postsurgical scarring by acting as a barrier to prevent blood from reaching tissue surfaces and forming adhesions. Postoperative joint swelling is reduced eliminating the inflammation which causes the joint to fill with fluids and recovery process is shortened by eliminating or minimizing post-surgical complications.

In joint replacement surgery the operating fluid contains up to 5000 ppm (one half of one weight percent) of PEO and up to 2½% weight percent of HPMC. The fluid is elastic and viscous to provide for good joint lubrication and acts as a cushioning agent between the bone and new artificial joint surfaces postsurgically until the natural synovial fluid has had a chance to replenish.

Synovial fluid is drained from two of the knee joints of 10 dogs. The knee joints of half of these dogs are injected with 3 mls. of a 5000 ppm PEO and 2½ weight percent HPMC solution. The joints of the other half of the dogs are injected with 3 mls of a saline solution as a control. The dogs are observed postoperatively at 12 hour intervals for two weeks. The dogs receiving the viscoelastic PEO HPMC solution have less swelling and heal faster than the control group.

Osteo arthritis is a degenerative bone disease characterized by the progressive loss of cartilage within the affected joint which allows hard bone surfaces to come in contact with one another and be worn away. Inflammation is caused by the underlying disease which leads to loss of joint lubrication which results in friction and more inflammation. Inflammation impedes normal tissue function and the cycle continues.

The viscoelastic composition of the invention acts as a cushioning agent to break the destructive cycle of inflammation and deterioration of tissue function with more inflammation and eventual cartilage destruction. The fluid acts as a cushion which allows the body to heal itself to eliminate the inflammation which probably initiated the destructive process. It is important that an effective cushioning agent does not cause post application swelling or joint blowout with a possible rupture of the joint capsule.

The fluid is injected into the joint, at six to nine month intervals.

Cortisone treatments have been used to treat inflamed joints, but because they mask the underlaying etiology, they simply serve to hasten the destuctive process.

In osteoarthritis the fluid must be more gelatinous. The fluid can contain from about 10 up to 5000 ppm PEO, from about 2 up to 2½ weight percent HPMC and from 5 up to 13 weight percent Pluronic F-127. This fluid provides excellent lubrication and cushioning for a prolonged period of time in order to reduce the joint inflammation and allow the body to begin a natural healing process. None of the animals receiving applications of the fluid in their joints exhibit an allergic reaction. An allergic reaction is frequently typified by the accumulation of water within the joint capsule postsurgically. The viscoelastic operating and cushioning fluids are also to used to impregnate artificial ligaments and tendons to prevent tissue ingrowth postoperatively.

The viscoelastic fluid has also been used to treat degenerative joint disease in horses. A 100 ppm PEO and 2½ percent by weight of HPMC mixture in a physiological saline solution (4 to 6 mls) was injected into the knee joints of horses. Lameness disappeared and the animals had symptomatic relief for up to nine months.

Spine and Neurosurgery

The viscoelastic medium of the invention may reduce or prevent any adhesions or scar tissue formation around the dura and nerve roots following laminectomy surgery. The viscoelastic medium acts as a barrier preventing blood from reaching the area which was operated on. The theory is that with no blood, there can be no scar tissue formation and no adhesion. The viscoelastic materials stays at the wound site long enough to allow healing to occur before allowing natural body fluids into the area.

In spine surgery, specifically a laminectomy, and in nerve surgery the solution may contain from about 20 up to 5000 ppm PEO, from about 1 to 2½ weight percent carboxymethyl cellulose and from about 5 up to 13 weight percent Pluronic F-127. The purpose of the fluid is to act as a barrier to prevent blood from entering or accumulating in the wound area and to act as a lubricant preventing the formation of wound adhesions or scar tissue between the exposed nerves and surrounding tissue in the wound area. Retention time is controlled by crosslinking.

Crosslinking may be accomplished using the following method:

1. Using the ingredients and weight percentages listed in Table 1, below, the carboyxmethyl cellulose, polyethylene oxide and Pluronic F-127 are mixed into the buffered physiological saline solution. When thoroughly mixed, the dimethylol urea crosslinking agent is added and, the ammonium chloride which acts as a catalyst is added to initiate the crosslinking reaction. The mixture is heated to 90° C. and held at this temperature for one hour. The resulting composition prevents or minimizes would adhesion.

TABLE 1

| Ingredient | Weight % |
|---|---|
| Polyethylene oxide | 0.5 |
| Carboxymethyl cellulose | 2.5 |
| Pluronic F-127 | 13.0 |
| Dimethylol urea | 0.25 |
| Ammonium chloride NH$_4$Cl | 0.025 |
| Buffered physiological saline | 83.725 |

The following animal trials in rabbits have established that scar formation is reduced with these solutions.

Surgical Procedures

This study was performed in 60 adult female New Zealand rabbits. However, because of post-surgical complications only 54 rabbits were used in data representation. After undergoing general anesthesia, each animal underwent the following procedure: (1) a medial incision was made along the spinous process to the lumbosacral region. After cutting through the skin and subcutaneous tissue, the fascia of the muscle was opened from the right of the spinous process. The muscles were pulled aside laterally to expose the spinous processes and vertebral arches. A small retractor was inserted into the wound and an oval defect of approximately 3×10 mm was drilled into the lamina with a dentist drill. A second similar laminectomy was made with one intact vertebra between the laminectomies. This second laminectomy served as a control site. Bone wax or Gelfoam was used to control excessive bleeding from the bone when required. One laminectomy site was coated with a standardized amount of one of the following agents: (1) 2% hydroxypropyl methylcellulose (10 ppm PEO); (2) 2% hydroxypropyl methylcellulose (20 ppm PEO); (3) Dextran 70(Hyskon); (4) 2% sodium carboxymethylcellulose; (5) 1% sodium carboxtmethylcellulose; and (6) sodium hyaluronate (Hylartin V). The other site received no treatment and thus served as a control. The wounds were then closed using a continuous 3-0 chromium catgut suture of 3-0 mercelene. For the sake of later orientation, a metal suture of 3-0 steel wire was placed in the muscle near the middle of the intact vertebra between the hemilaminectomies.

The animals were allowed to recover from surgery and returned to their individual cages. At four weeks and eight weeks following surgery one-half of the rabbits were sacrificed, the spinal column cut at both ends of the operative area to include the excised vertebra in their entirety and the entire specimen immersed in 10% neutral buffered formalin.

Histological Analysis

Histological analysis was performed on decalcified specimens. After decalcification in 10% formic acid formalin solution for two weeks, specimens were cut in the middle of the intact vertebra between laminectomies. The specimens (both control and test) were reduced in size and left to decalcify for two more weeks. Specimens were then embedded in paraffin and four 10 um sections were cut so that the plane of the surface included the graft material with the spinal cord in the microscopical section. Staining was accomplished with hematoxylin-eosin for all groups. All sections for each specimen were examined. However, the qualitative assessment was performed on what was considered to be the best cut section from the group. This assessment consisted of a microscopic examination of the surgical site. Particular attention was paid to how much scar tissue was present on the dura and whether the scar tissue extended into the surgical site. Another parameter that was evaluated was the size of the laminal defect and whether the surgical gap had reduced in size. The number and type of cellular detail at the surgical site (i.e. osteoblast (bone), fibroblasts and lymphocytes (scar tissue) and chondrocytes (collegen synthesis)) were also noted.

Results

Only the data for the four week specimens are summarized. This was done since eight week specimens, which healed more completely than the four week specimens, invariably demonstrated no significant change from the four week specimens with respect to whether the control or treated site demonstrated the least amount of scar tissue. Therefore, based on visual observation a value of 0 was assigned to each animal if the treated site appeared comparable in healing to the control site, —if the control site appeared better healed than the treated site, and a +if the treated site appeared best.

Utilizing this grading scale, it is apparent from Table 1 that both 1% and 2% CMC appeared to afford the best prevention of extensive scar formation. It should be noted that in no specimens was there any histological evidence of healing totally devoid of scar tissue. This assessment therefore, more accurately reflects the degree to which scar tissue was present relative to all the other specimens.

TABLE 1

| Rabbit # | Group | Evaluation | Notes |
|---|---|---|---|
| N112 | Hyskon | + | |
| N113 | Hyskon | − | |
| N114 | Hyskon | + | |
| N129 | Hyskon | + | |
| N200 | 87094-V* | − | macrophages present @ treated site |
| N201 | 87094-V | − | |
| N202 | 87094-V | + | |
| N203 | 87094-V | + | |
| N256 | 87093-IO** | + | |
| N257 | 87093-IO | − | |
| N255 | 87093-IO | + | |
| N258 | 87093-IO | − | |
| N259 | 87093-IO | 0 | |
| Q139 | 2% CMC | − | |
| Q140 | 2% CMC | + | |
| Q135 | 2% CMC | ++ | 1 week specimen |
| Q136 | 2% CMC | + | |
| Q127 | 2% CMC | − | |
| Q133 | 1% CMC | + | |
| Q134 | 1% CMC | + | numerous chondrocytes present |
| P668 | 1% CMC | ++ | same as Q134 |
| P669 | 1% CMC | + | possible soft tissue inflammation response |
| P743 | 1% CMC | 0 | |
| P751 | Hylartin | 0 | numerous chondrocytes |
| Q374 | Hylartin | − | |
| Q375 | Hylartin | − | |
| Q378 | Hylartin | − | numerous chondrocytes |
| Q377 | Hylartin | 0 | same as Q378 |

*2% HPMC, 10 ppm PEO
**2% HPMC, 20 ppm PEO

Neurosurgical applications of the fluids are similar to the spinal applications. Namely, the elimination or reduction of scar tissue formation in and around the brain post operatively. The "barrier" effect is the mode of operation by which the fluid achieves its purpose.

The anti-adhesion properties of these fluids are useful in several other areas of surgery where it is important to reduce scar formation. These surgical areas include abdominal surgery, thortic and cardio-vascular surgery and ob/gyn.

Urology

In connection with urology the viscoelastic fluid includes an operating fluid and a postsurgical cushioning fluid. The operating fluid facilitates the introduction of instruments into the urethra, bladder and ureters and enhances the surgeons visualization, while it protects sensitive tissue from damage and instrument contact. The viscoelastic operating fluid also expands the diameter of narrow passageways and as a tamponade against unwanted accumulation of blood. In addition, the viscoelastic fluid of the invention facilitates the passage of urinary stones and fragments through the ureters because of the lubricating properties of the fluid. The urology operating fluid is composed of up to 500 ppm PEO and 1 to 2 weight percent of HPMC. A composition of 3 mls of a physiological solution having 500 ppm of PEO and 2 weight percent of HPMC is injected into the ureter of five cats having kidney stones (urinary calculi) and facilitate passage of urinary calculi. It also acts as a lubricant and inflates the diameter of the ureter. The fluid may be used alone or with lithotrophsy (ultrasonic fragmentation of the stone). The solution has been shown to dissolve the calculi and reduce reoccurrence in cats.

The urological cushioning fluid reduces postoperative inflammation pain and speeds patient recovery. About 2 mls of 1000 ppm PEO and 2 weight percent HPMC in physiological saline solution was applied to the postoperative area following urological surgery. Minimal scar and adhesion formation were observed. The same results are observed following transurethral resection and no inflammation occured.

About 0.5 mls of 40 ppm PEO and 2 weight percent HPMC in a physiological solution was injected into the ureter of five cats having urinary calculi. The calculi passed spontaneously. No reoccurrance of stones were found 12 months after treatment.

Thus it can be seen from the preceding examples that compositions having a polyethylene oxide content of 10 ppm to 500 ppm are therapeutically useful in treating disease as well as in preventing injury.

Plastic surgery

A viscoelastic a gel fluid of the present invention is used to replace the silicone gel fluids in all silicone implants. Such implants include mammary implants for cosmetic or reconstruction purposes, testicular implants, penile implants, small "pillow" implants and so on. The viscoelastic fluid is used separately as an anti-adhesion agent to act as a slippery barrier to prevent contact between the implant and healing tissue. The implantable fluid is composed of from about 2 up to 3 weight percent HPMC for high viscosity and from about 10 up to 50 ppm of PEO for moderate elasticity. This fluid is placed in a silicone shell and is implanted within the body. The shell is also coated with the fluid. Following implantation no inflammation or adhesion is observed. Crosslinking in a manner similar to that described for the wound adhesion prevention preparation is used to increase the cohesiveness of the fluid.

Crosslinking may be performed as follows:
1. Using the ingredients and weight percentages listed in Table 2 below, the hydroxylpropyl methylcellulose and polyethylene oxide are mixed into the buffered saline solution. When thoroughly mixed, the formaldehyde urea crosslinking agent is added. Then the ammonium chloride which sets as catalysyt is added to initiate the crosslinking reaction. The mixture is heated for one hour at 90° C. The resulting composition is an inert gel fil which will not bleed through a prosthetic shell.

TABLE 2

| Ingredients | Weight % |
|---|---|
| Polyethylene oxide | .005 |
| Hydroxypropylmethylcellulose | 3.0 |
| Formaldehyde urea | 0.2 |
| Ammonium chloride | 0.02 |
| Buffered physiological saline | 96.775 |

Variations and modifications can of course be made without departing from the spirit and scope of the invention.

What is claimed is:

1. A method of irrigating and protecting the corneal tissues during opthalmic surgery which comprises:
   (a) covering the inner cornea with a physiologic saline solution comprising about 2% hydroxypropylmethyl cellulose and about 10 ppm polyethylene oxide.
   (b) simultaneously wetting the outer cornea with a physiologic saline solution comprising about half the hydroxypropylmethyl cellulose and about twice the polyethylene oxide of the solution of step (a); and
   (c) further, during the surgery, periodically wetting the outer cornea with the solution of step (b).

* * * * *